United States Patent
Kuo et al.

(10) Patent No.: US 7,712,198 B2
(45) Date of Patent: May 11, 2010

(54) MICRONEEDLE ARRAY DEVICE AND ITS FABRICATION METHOD

(75) Inventors: Shih-Chi Kuo, Yangmei Township, Taoyuan County (TW); Yu-Kon Chou, Sindian (TW)

(73) Assignee: Industrial Technology Research Institute, Hsinchu (TW)

( * ) Notice: Subject to any disclaimer, the term of this patent is extended or adjusted under 35 U.S.C. 154(b) by 171 days.

(21) Appl. No.: 11/754,368

(22) Filed: May 29, 2007

(65) Prior Publication Data
US 2007/0233016 A1    Oct. 4, 2007

Related U.S. Application Data

(62) Division of application No. 10/994,105, filed on Nov. 19, 2004, now abandoned.

(30) Foreign Application Priority Data
Jul. 16, 2004   (TW) ............................... 93121337 A

(51) Int. Cl.
*B23B 37/00* (2006.01)
(52) U.S. Cl. .................... 29/17.3; 29/17.5; 29/17.9; 29/527.2; 216/39; 264/221; 604/890.1; 604/173
(58) Field of Classification Search ............... 29/17.3, 29/527.1, 17.5, 17.9, 527.2; 216/11, 39; 604/890.1, 272, 173, 27, 290; 264/221
See application file for complete search history.

(56) References Cited

U.S. PATENT DOCUMENTS

| | | | |
|---|---|---|---|
| 6,551,849 B1 * | 4/2003 | Kenney | 438/34 |
| 6,663,820 B2 * | 12/2003 | Arias et al. | 264/496 |
| 6,924,087 B2 * | 8/2005 | Yeshurun et al. | 430/313 |
| 7,285,113 B2 * | 10/2007 | Yeshurun | 604/272 |
| 2002/0082543 A1 * | 6/2002 | Park et al. | 604/21 |
| 2005/0011858 A1 * | 1/2005 | Kuo et al. | 216/17 |
| 2006/0084942 A1 * | 4/2006 | Kim et al. | 604/890.1 |

* cited by examiner

*Primary Examiner*—David P Bryant
*Assistant Examiner*—Christopher M Koehler

(57) ABSTRACT

A microneedle array device and its fabrication method are provided. The microneedle array device comprises a supporting pad and a plurality of microneedles. Each microneedle has a top portion with a via thereon, thereby the microfluid may flow in or out. The intersection between the top portion and the inner tube of a microneedle forms a convex needle structure, and is almost perpendicular to the upper surface. For each microneedle, a hollow closed tube is formed between the top portion and the supporting pad. The fabrication method uses substrates with high transmittance and a plurality of convex area thereon as upper and lower caps, and applies a photolithography process to fabricate a microneedle array mold. It then sputters or electroplates metal material on the mold. The microneedle array is formed after having taken off the mold.

17 Claims, 17 Drawing Sheets

US 7,712,198 B2

MICRONEEDLE ARRAY DEVICE AND ITS FABRICATION METHOD

CROSS-REFERENCES TO RELATED APPLICATIONS

This is a division of U.S. patent application Ser. No. 10/994,105, filed Nov. 19, 2004 now abandoned.

FIELD OF THE INVENTION

The present invention generally relates to a microneedle array structure, and more specifically to a microneedle array device, and a method of forming the same.

BACKGROUND OF THE INVENTION

The current microneedle array may be made of silicon (Si substrate), metal or polymer. The manufacturing methods of Si substrate microneedle array can further be categorized as using wet etching or dry etching. The manufacturing process of metal microneedle array can further be categorized as using electroplating or deposition. The manufacturing process of polymer microneedle array can be further categorized as using molding or photolithography.

Among the methods of microneedle array, the most widely adopted is using Si substrate to fabricate the hollow needles or mold. However, the fabrication process of using Si substrate is more complicated, as disclosed in WO0217985, and requires many steps of wet/dry etching and thin film deposition. As it takes a longer time to fabricate, the yield rate is low and the cost is high. U.S. Pat. No. 6,334,856 disclosed a method of fabricating a microneedle array having flat needle tips and tapered tubes, as shown in FIG. 1. This type of design limits the width of the flow channel and the flexibility of the needle. To fabricate the needle higher than 100 um, the needle density must be restricted in compromise for an appropriate size of aperture and strength of needle structure. The restriction of low needle density further causes the problem of insufficient sampling. In addition, the Si substrate microneedles are brittle and break easily.

The tip of the hollow microneedle in most prior arts is designed as flat, except the design disclosed in WO0217985 (see FIG. 2), which is a slant. This is because a slant tip is easier to penetrate the human skin for micro-sampling than the flat tip, as the human skin is flexible.

Kim et al. disclosed a method for fabricating metal microneedle array in Journal of Micromechanics and Micro engineering in 2004. They spread two layers of SU-8 on a glass substrate and used a back exposure to seperately bake the two layers of SU-8. They also used reactive ion etching to obtain an SU-8 pillar array structure, and then used sputtering, electroplating, planarization and polishing to fabricate a tapered metal hollow microneedle array, as shown in FIG. 3. However, the method requires multiple layers of SU-8 to achieve the layered effect and the high aspect ratio of the pillar is prone to slant or twist. The fabrication process is difficult to maintain the quality.

U.S. Pat. No. 6,663,820 disclosed another method of using lithography and photolithography to fabricate polymer microneedle array, as shown in FIG. 4. This method has the advantages of rapid fabrication of micromold and microneedle, and low fabrication cost of the material and process. However, the flat-tip microneedles are still limited in the application. In addition, the polymer microneedles of this method do not have microchannels or reservoirs, and require additional fabrication process to attach the microchannels and reservoirs, if necessary. It is, therefore, difficult to have this method applied for mass production.

Numerous methods of fabricating microneedle array have been proposed. Regardless of the material used, the object of the microneedle array includes the capability to penetrate the human skin for micro-injection or micro-sampling painlessly, easy to fabricate, low in fabrication cost and safe to use.

SUMMARY OF THE INVENTION

The present invention has been made to overcome the aforementioned drawback of conventional bonding methods of fabricating microneedle array. The primary object of the present invention is to provide a microneedle array device, including a supporting pad and a plurality of microneedles. The supporting pad has an upper surface. Each microneedle has a slant or concave top portion with a via thereon, thereby the microfluid may flow in or out. The intersection between the top portion and the inner tube of a microneedle forms a convex needle structure. Each microneedle stands on the upper surface of the supporting pad and is almost perpendicular to the upper surface. A hollow closed tube is formed between the top portion and the supporting pad.

The supporting pad further includes a bottom portion and at least a layer of reservoir. The reservoir is located above the bottom portion and below the microneedle. The reservoir can be further divided, if necessary, into a plurality of reservoir units, with reservoir units separated from one another to prevent the microfluid flowing from one unit to another. The monolithic metal structure of the present invention includes convex needle structure formed by the intersection of the slant or concave top portion of each microneedle and the inner tube of a microneedle. The main feature of the present invention includes the safety of use and the reduction of pain when the microneedles are used. Furthermore, the rigidity and the slant uniformity of the microneedle with slant top portion are both improved so that it is suitable for molding and mass production.

Another object of the present invention is to provide a method of fabricating a microneedle array device, including the steps of: (1) providing a substrate, and forming a plurality of concave areas on a surface of the substrate; (2) spreading a layer of photo-sensitive material on the substrate and covering a layer of light transmission material on top of the photo-sensitive material; (3) using a patterned mask for exposing and lithographic processing of the photo-sensitive material on the light transmission material to obtain a polymer hollow microneedle array mold based on the light transmission material; and (4) using the polymer hollow microneedle array mold to form a microneedle array device.

According to the present invention, there are several techniques to be used in step (1) of forming a plurality of concave areas, including etching, X-ray photo-etching, ultra-violet etching, ion beam etching and excimer laser micromachining. Step (4) of the method further includes the following sub-steps: (4a) coating a layer of metal on the outer surface of the polymer hollow microneedle array mold and the light transmission material to form a microneedle array; and (4b) removing the polymer hollow microneedle array mold from the microneedle array. In step (4), the techniques for coating metal to the surface of the polymer hollow microneedle array mold include electroplating, electroless plating, evaporation, and sputtering. The metal used can be Cu, Cr, Ni, Fe, Au, Pt, Pd, stainless steel and their alloys. The present invention uses the coating of photo-sensitive polymer on the concave areas of the substrate and covering with a light transmission material, which is exposed to define an outline of the microneedle and using lithography to obtain a polymer hollow microneedle array mold using the high light transmission material as the base for further fabrication of a metal microneedle array. The advantages of the fabrication method of the present invention are simple process and low in cost.

The foregoing and other objects, features, aspects and advantages of the present invention will become better understood from a careful reading of a detailed description provided herein below with appropriate reference to the accompanying drawings.

BRIEF DESCRIPTION OF THE DRAWINGS

FIGS. 11A-11K show the fabrication method of the second embodiment of the present invention.

DETAILED DESCRIPTION OF THE PREFERRED EMBODIMENTS

Figure 1:
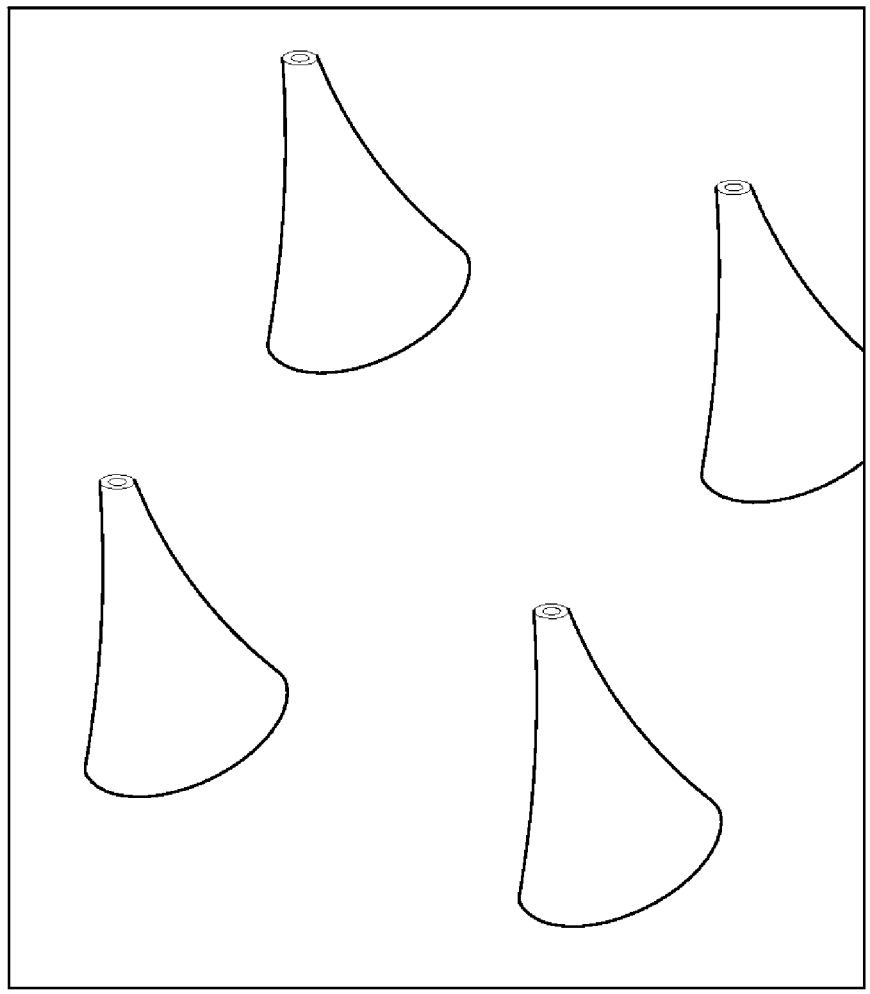
FIG. 1 shows a conventional flat-top microneedle array made of Si substrate.
Figure 2:
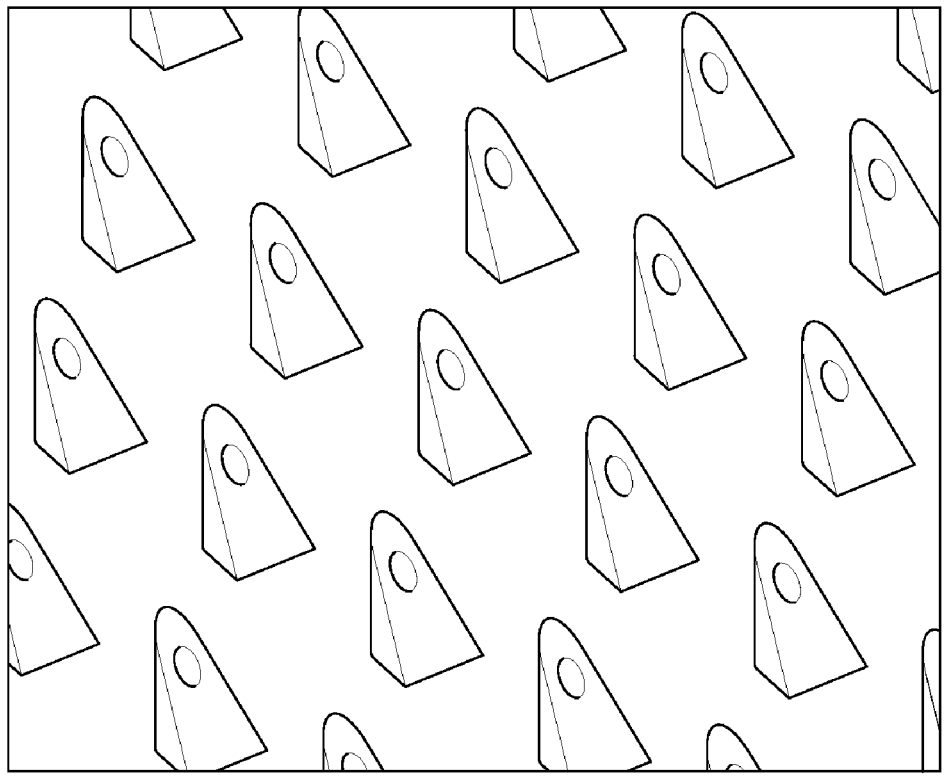
FIG. 2 shows a conventional slant top microneedle array made of Si substrate.
Figure 3:
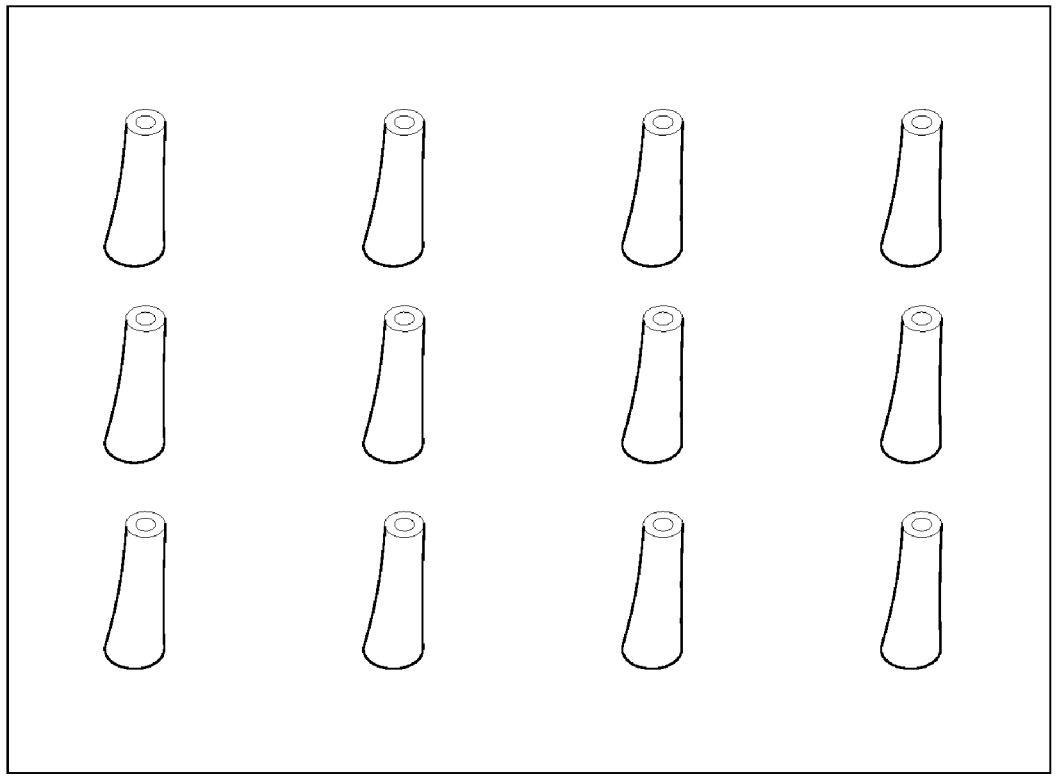
FIG. 3 shows a conventional flat-top microneedle array made of metal.
Figure 4:
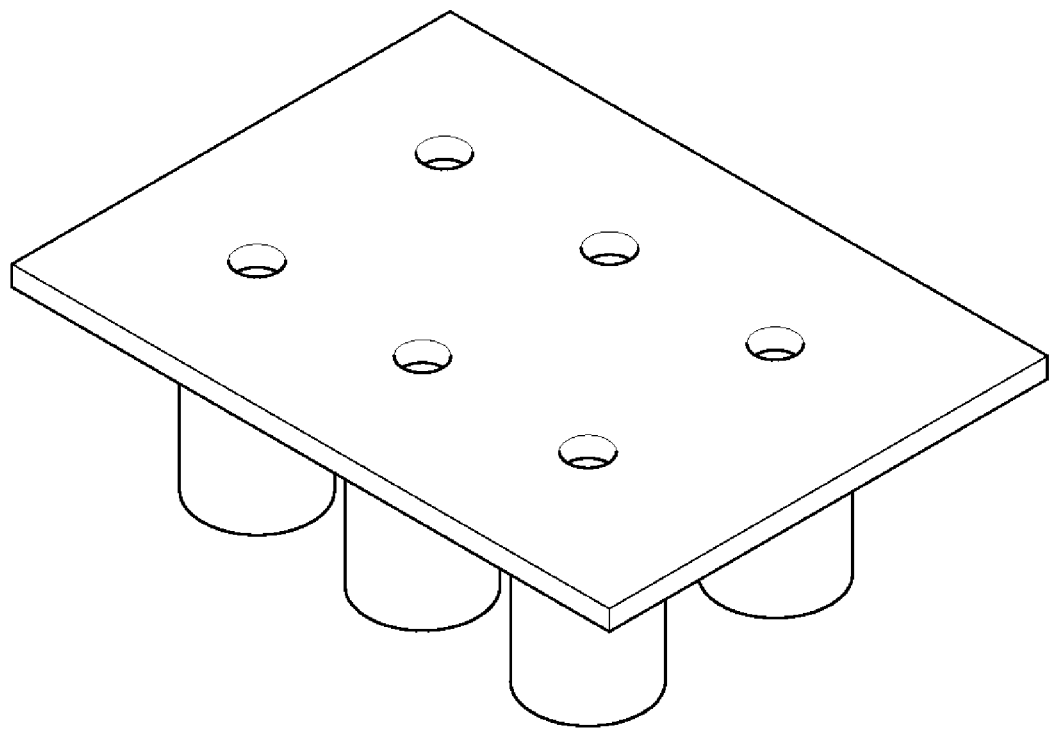
FIG. 4 shows a conventional flat-top microneedle array made of polymer.
Figure 5A:
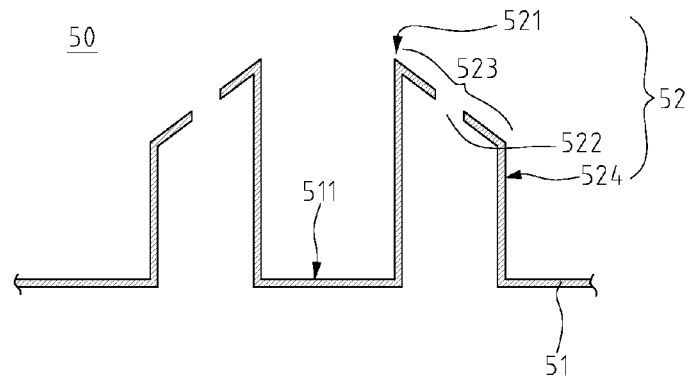
FIG. 5A shows a cross-sectional view of the first embodiment of a microneedle array device of the present invention.
Figure 5B:
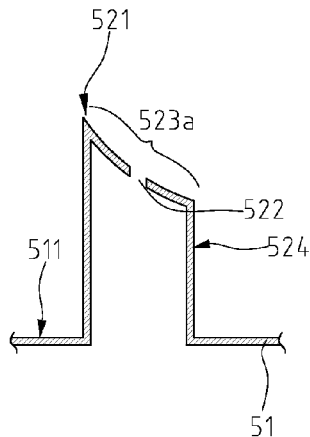
FIG. 5B shows a schematic view of the concave top of a microneedle of the present invention.

FIG. 5A shows a cross-sectional view of a microneedle array device 50 of the present invention. As shown in FIG. 5A, microneedle array device 50 includes a supporting pad 51 and a plurality of microneedles 52. Supporting pad 51 includes an upper surface 511. For the purpose of safety and effective skin penetration, the top portion of each microneedle 52 includes a convex needle structure 521. The top portion of microneedle 52 can be a slant 523 or a concave surface 523a, as shown in FIG. 5B. The top portion of microneedle 52 intersects with tube wall 524 to form convex needle structure 521. In addition, top portion 523 or 523a includes a via 522, which allows the follow of a microfluid, for example, a medicine to flow out or a blood to flow in. According to the present invention, the microneedle array is a monolithic metal structure with each microneedle 52 standing on and perpendicular to the upper surface 511 of supporting pad 51, and a hollow closed tube being formed between top portion 523 (523a) and supporting pad 51.

Figure 5C:
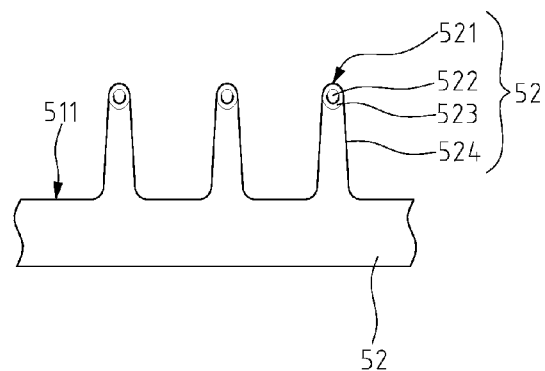
FIG. 5C shows a schematic view of the first embodiment of a microneedle array device of the present invention.
Figure 6A:
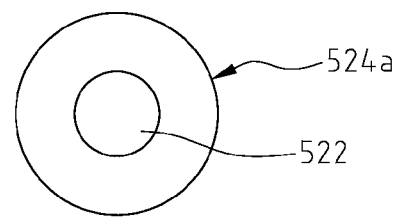
FIGS. 6A and 6B show respective top views of the microneedles having different inner tube shapes.
Figure 6B:
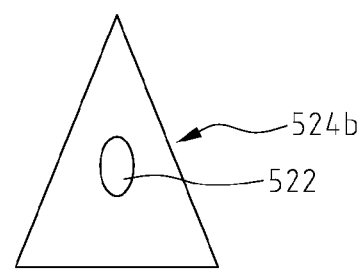

FIG. 5C shows a schematic view of the structure of microneedle array device 50 of the present invention. The top portion 523 of each microneedle 52 is a slant, and the cross-section of tube wall 524 forms a closed oval, circular, or triangular shape, as shown in FIG. 6A and FIG. 6B, respectively. The metal for fabricating microneedle array can be Cu, Cr, Ni, Fe, Au, Pt, Pd, stainless steel, or their alloys. The range of the aperture of each microneedle is 10-70 um, the outer circumference is 80-250 um, and the height is 100-600 um.

FIGS. 7A-7J show the fabrication method of the first embodiment of the present invention. First, a substrate is provided, including a plurality of concave areas on the surface. According to the present invention, there are several techniques for forming a plurality of concave areas, including etching, X-ray photo-etching, ultra-violet etching, ion beam etching and excimer laser micromaching. The present embodiment uses an anisotropic wet etching for explanation.

Figure 7A:
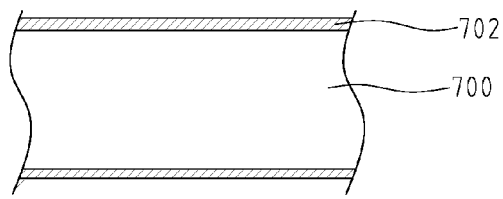
FIGS. 7A-7J show the fabrication method of the first embodiment of a microneedle array device of the present invention.
Figure 7B:
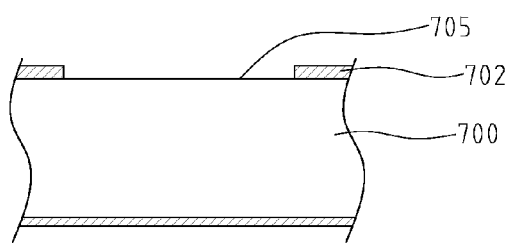
Figure 7C:
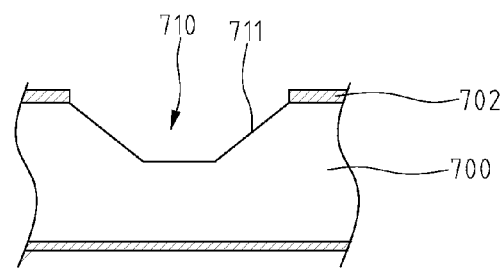
Figure 8A:
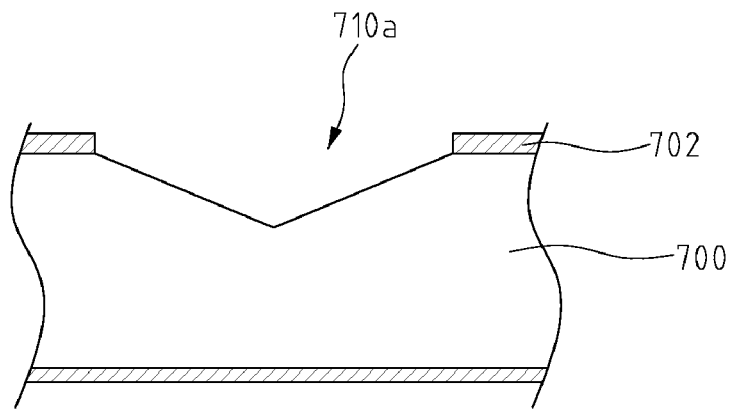
FIGS. 8A and 8B show respective top cross-sectional views of the different shapes of concave areas of Si substrate of the present invention.
Figure 8B:
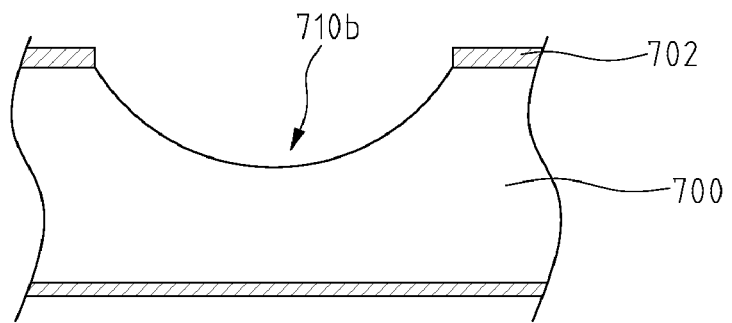

As shown in FIG. 7A, a single crystal silicon with a grain-orientation [1,0,0] is used as a substrate 700, and a protective layer 702 is deposited on the surface. Protective layer 702 can be made of $Si_3N_4$. The wet etching areas 705 are defined, as shown in FIG. 7B, followed by wet etching. The solution commonly used in silicon anisotropic wet etching includes potassium hydroxide (KOH) and Tetra-methyl-ammonium hydroxide (TMAH). After etching the silicon, a plurality of concave areas 710 are formed. Each concave area 710 has two slants 711, as shown in FIG. 7C. Slant 711 defines a slant top 523 of each microneedle. The shape of the plurality of concave areas can vary in accordance with the fabrication process, for example, a V-shape 710a or U-shape 710b, as shown in FIG. 8A and FIG. 8B, respectively. In other words, a U-shaped concave area 710 defines a concave curvy top portion 523a of a microneedle.

Figure 7D:
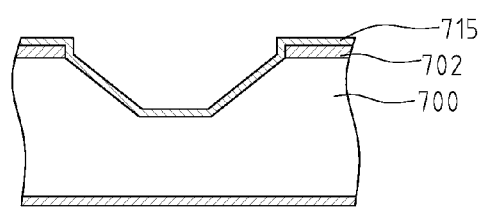

Before the coating of photo-sensitive material 720, a sacrificial layer or mold release layer 715 is coated on top of substrate 700 for the subsequent mold release, as shown in FIG. 7D. The commonly used material for the sacrificial or mold release layer includes SU-8, Al, Au, silicon rubber and Teflon.

Figure 7E:
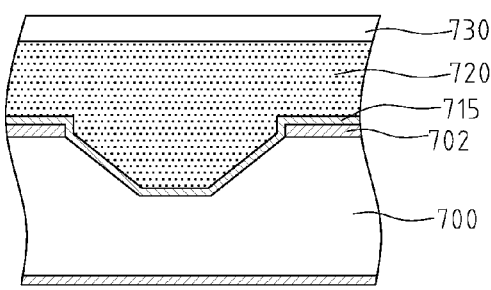

The next step is to spread a photo-sensitive material 720 on top of sacrificial layer 715, and a light transmission material 730 on top of photo-sensitive material layer 720, as shown in FIG. 7E. Photo-sensitive material 720 used in the present invention is SU-8, a negative photo-resist developed by Microlithography Chemical Corporation (USA), or JSR 430N, a positive or negative photo-resist developed by Japanese Synthetic Rubber (Japan). Light transmission material can be either glass or PMMA.

Figure 7F:
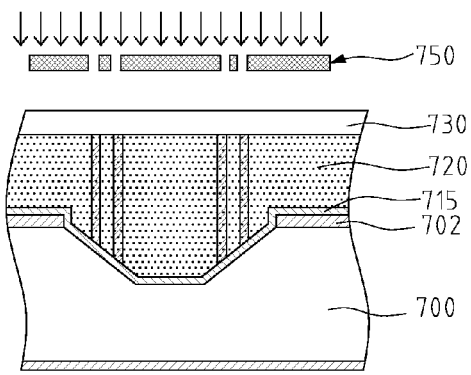
Figure 7G:
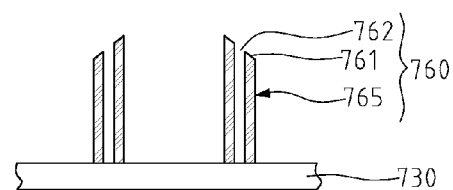
Figure 7H:
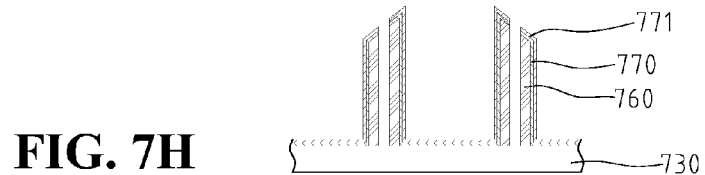
Figure 7I:
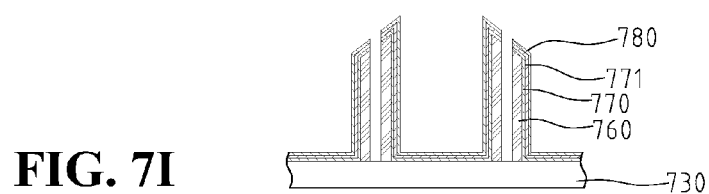

The next step is exposure and lithography to obtain a polymer hollow microneedle array mold 760 using light transmission material 730 as a base. As shown in FIG. 7F, a patterned mask 750 defining the shape of tube wall 524 and via 522 of microneedle 52 is used before the exposure. The shapes can be either oval, circular 524a, or triangular 524b, as shown in FIG. 5C, FIG. 6A, and FIG. 6B, respectively. If SU-8 negative photo-resist is used as photo-sensitive material 720, the bond forms at a later stage of the exposure to light and stays during the development. The un-exposed part is dissolved. After the mold release, a polymer hollow microneedle array mold 760 having a plurality of polymer microneedles is obtained for subsequent metal plating, as shown in FIG. 7G. Because the present invention directly applies photo-sensitive material 720 on the slant of concave areas 710 on substrate or the concave curvy top, the top portion 761 of polymer microneedle 765 is also slant or concave curvy surface. Microneedle 765 has a via 762 reaching light transmission material 730.

Figure 7J:
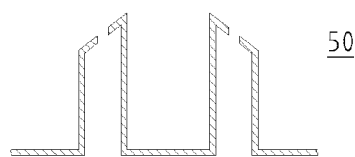

Finally, polymer hollow microneedle array mold 760 is used to form a microneedle array device 50, as shown in FIG. 7J. The forming of a microneedle array device step further includes the following two sub-steps: (a) coating a metal layer 780 on the outer surfaces of polymer hollow microneedle array mold 760 and light transmission material layer 730 to form a microneedle array device 50, and (b) removing polymer hollow microneedle mold 760 from microneedle array device 50.

Similarly, before the coating of metal layer 780 in sub-step (a), a sacrificial layer or mold release layer 770 is deposited on the outer surfaces of polymer hollow microneedle array mold 760 and light transmission material layer 730, and a starting layer 771 (FIG. 7H) is electroplated to electro-cast. The material for sacrificial layer 770 includes either Cu, Al, or Au. The material for starting layer 771 is any metal.

In sub-step (a), the electroplating, electroless plating, evaporation and sputtering is used to plate metal layer 780 on the upper surface (FIG. 7I) of strating layer 771. The metal for plating metal layer 780 may include Cu, Cr, Ni, Fe, Au, Pt, Pd, stainless steel, and their alloys.

In sub-step (b), the technique for removing polymer hollow microneedle array mold 760 from microneedle array device 50 is to remove sacrificial layer 770 deposited on the outer surfaces of polymer hollow microneedle array mold 760 and light transmission material layer 730. The technique includes oxygen plasma removal, thermal removal, solvent removal, aqueous removal or photo-degradation removal.

Figure 9A:
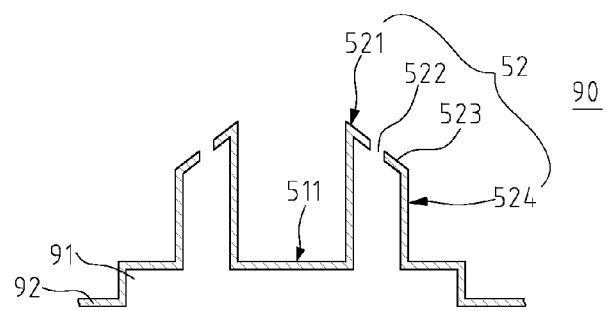
FIG. 9A shows a cross-sectional view of the second embodiment of a microneedle array device of the present invention.
Figure 10A:
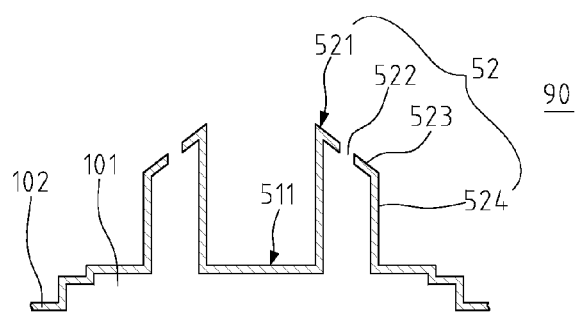
FIG. 10A shows a cross-sectional view of the third embodiment of a microneedle array device of the present invention.

FIG. 9A and FIG. 10A show the second and the third embodiments of a microneedle array device of the present invention, respectively.

Figure 9B:
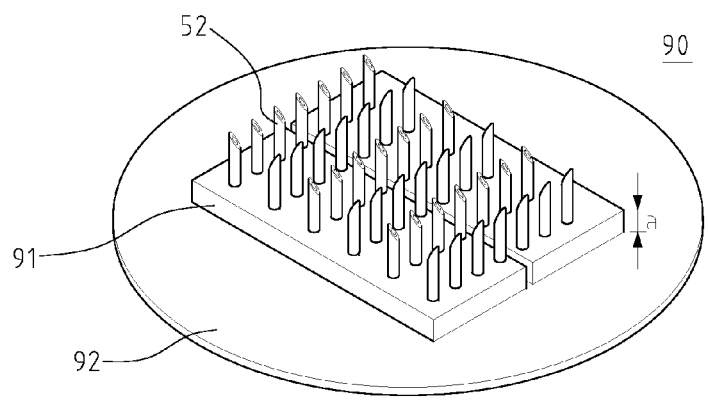
FIG. 9B shows a schematic view of the second embodiment of a microneedle array device of the present invention.
Figure 9C:
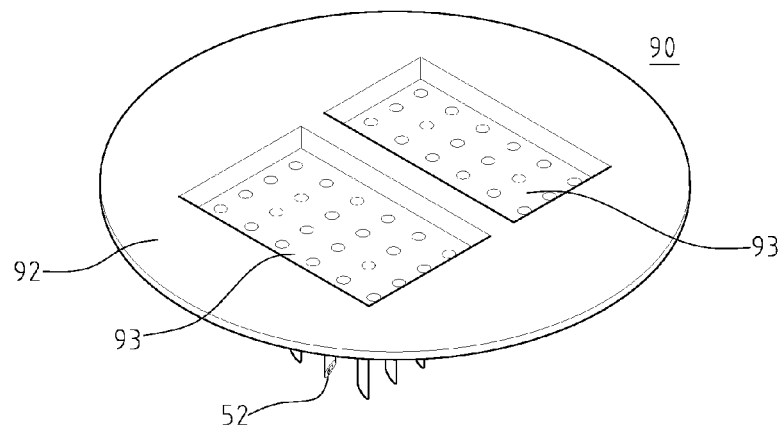
FIG. 9C shows a top view of FIG. 9B.

FIG. 9A is similar to the structure shown in FIG. 5A. The difference lies in microneedle array device 90 in FIG. 9A that has a reservoir layer 91 below a plurality of microneedles 52 and above bottom portion 92. Reservoir layer 91 is for storing or mixing the medicine or collecting blood sample. As shown in FIG. 9B and FIG. 9C, reservoir 91 may be further divided into a plurality of reservoir unit 93. Reservoir units 93 are separate from one another to block the flow of microfluid. They may be used for blood analysis.

Figure 10B:
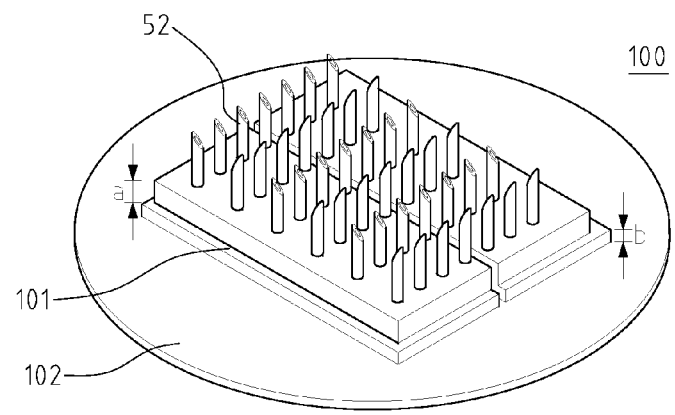
FIG. 10B shows a schematic view of the third embodiment of a microneedle array device of the present invention.
Figure 10C:
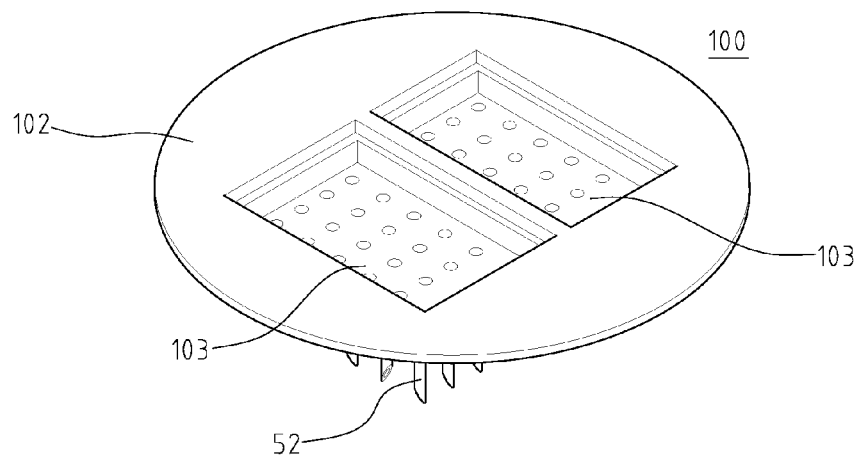
Figure 11A:
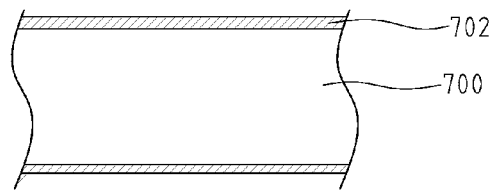
Figure 11B:
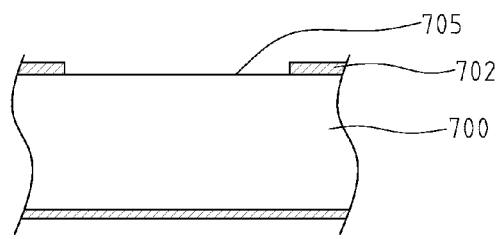
Figure 11C:
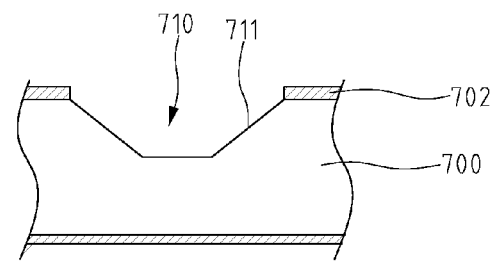
FIG. 11C shows a top view of FIG. 10B.
Figure 11D:
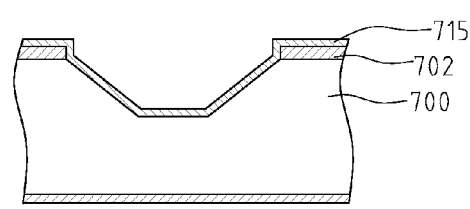
Figure 11E:
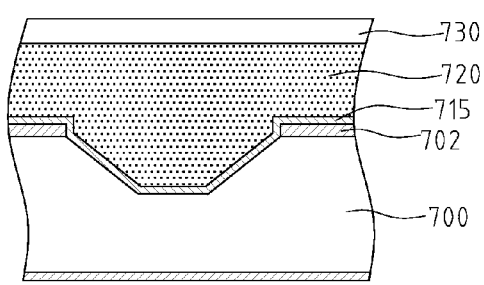
Figure 11F:
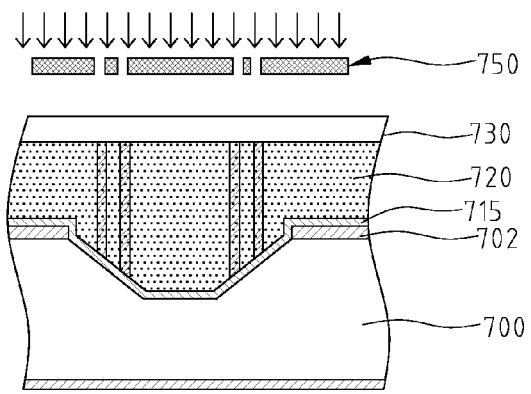
Figure 11G:
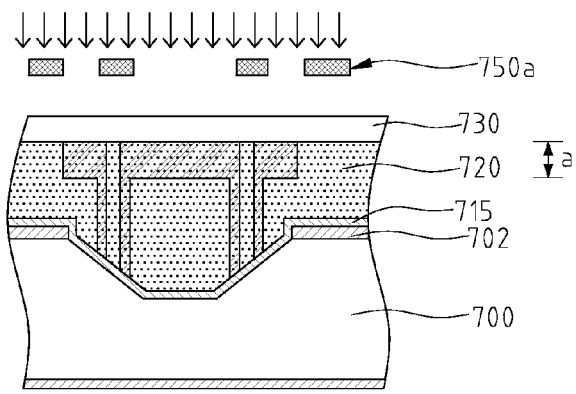
Figure 11H:
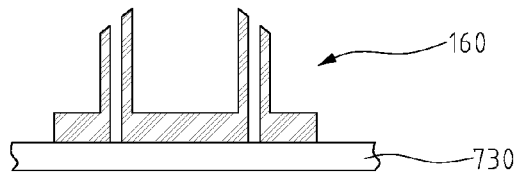
Figure 11I:
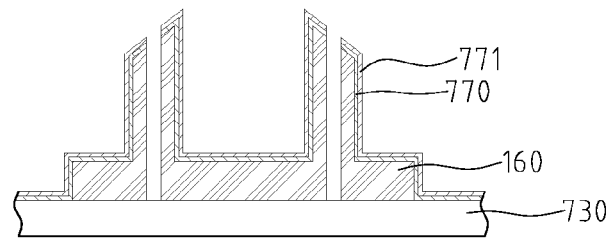
Figure 11J:
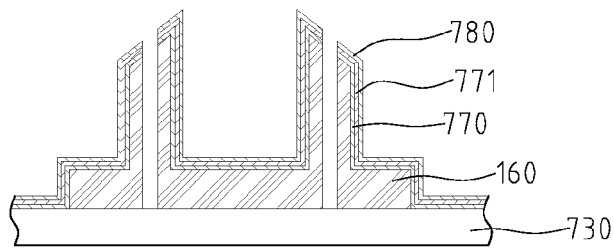
Figure 11K:
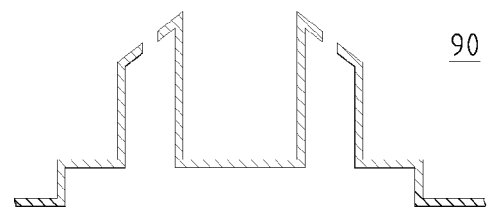
Figure 12A:
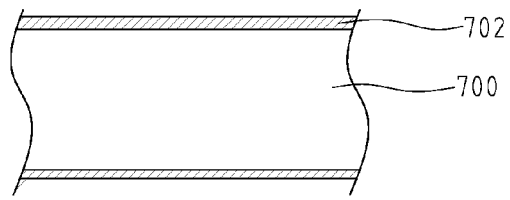
FIGS. 12A-12L show the fabrication method of the third embodiment of the present invention.
Figure 12B:
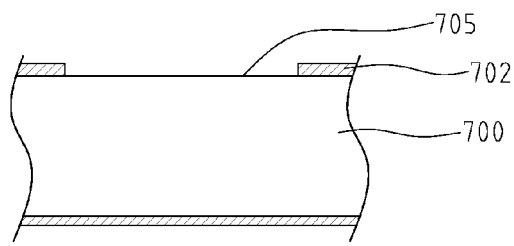
Figure 12C:
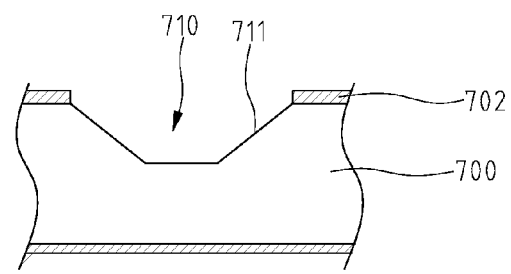
Figure 12D:
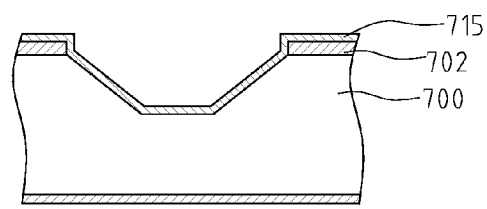
Figure 12E:
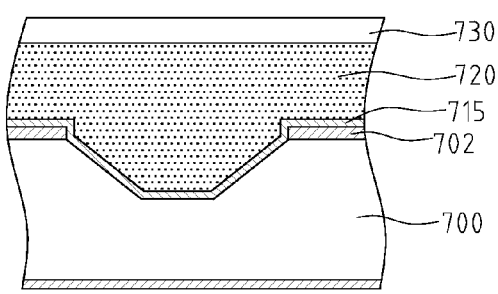
Figure 12F:
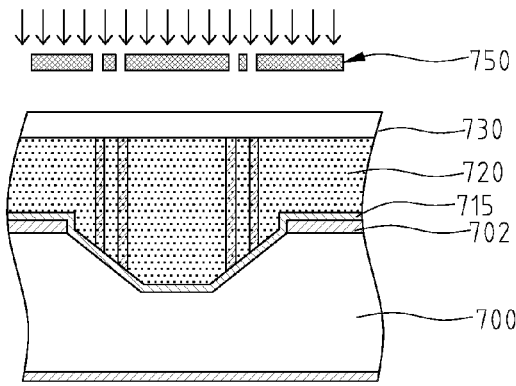
Figure 12G:
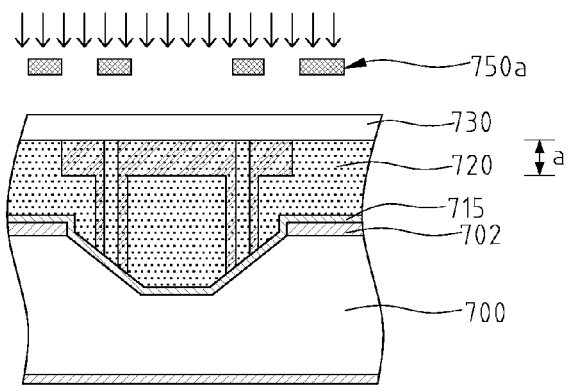
Figure 12H:
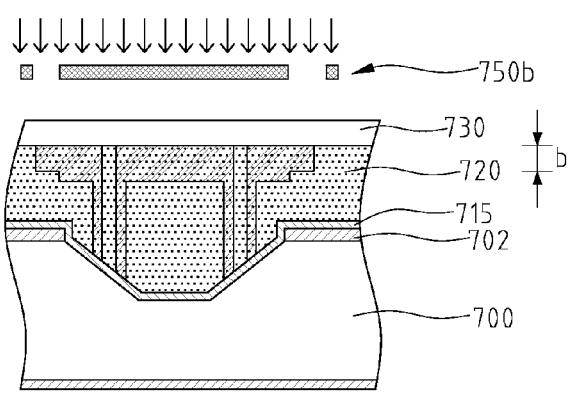
Figure 12I:
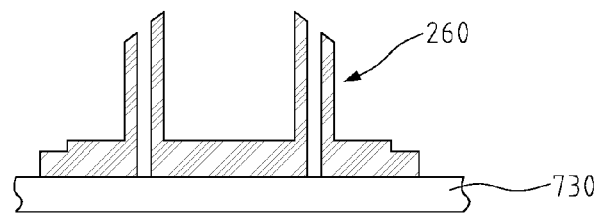
Figure 12J:
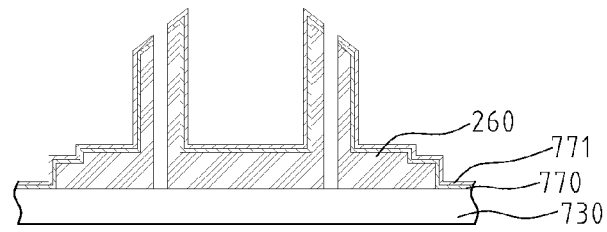
Figure 12K:
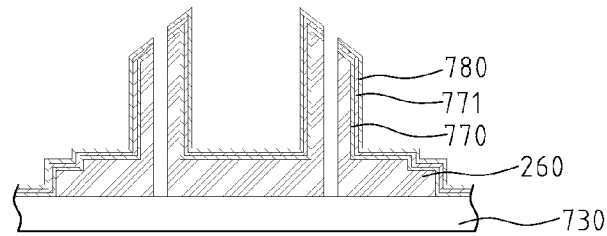
Figure 12L:
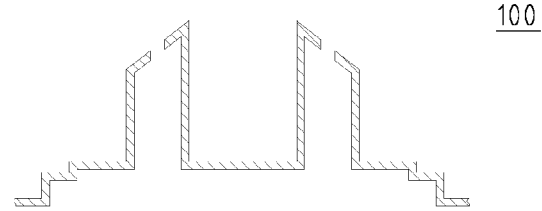

Similarly, microneedle array device 100 in FIG. 10A has two reservoir layers 101 below a plurality of microneedles 52 and above bottom portion 102. Reservoir layer 101 is for storing or mixing the medicine or collecting blood sample. As shown in FIG. 10B and FIG. 10C, reservoir layers 101 may be further divided into a plurality of reservoir unit 103. Reservoir units 103 are separate from one another to block the flow of microfluid.

FIGS. 11A-11K show the fabrication method of the second embodiment of the present invention.

The fabrication method of the second embodiment is similar to that of first embodiment. The only difference is in the exposure and development step. Because the second embodiment has a reservoir layer 91 in the structure, the second embodiment requires an additional exposure than the first embodiment. During the second exposure, a corresponding patterned mask 750a is used to define reservoir layer 91 and the shape of reservoir units 93 within. By adjusting the exposure dosage to control the depth "a" of the reservoir layer, the result of this step is to obtain a polymer hollow microneedle array mold 160. The remaining steps of the fabrication are identical to those in FIG. 7A-7J.

FIGS. 12A-12L show the fabrication method of the third embodiment of the present invention.

The fabrication method of the third embodiment is also similar to that of first embodiment. The only difference is still in the exposure and development step. Similarly, because the third embodiment has two more reservoir layers 101 in the structure, the third embodiment requires two additional exposures than the first embodiment. During the second and third exposures, a corresponding patterned mask 750a, 750b is used to define, respectively, each reservoir layer 101 and the shape of reservoir units 103 within. By adjusting the exposure dosage to control the depths "a" and "b" of the reservoir layers, the result of this step is to obtain a polymer hollow microneedle array mold 260. Therefore, according to the present invention, the first exposure is to form the shape and the structure of the microneedles, and the second and subsequent exposures are for forming the shape and the structure of the reservoir layer. The remaining steps of the fabrication are identical to those in FIG. 7A-7J.

In summary, compared to the other molding techniques, the present invention directly applies photo-sensitive polymer on the concave areas of the substrate to form a polymer hollow microneedle array mold having slants and concave curvy surface. Then, the polymer hollow microneedle array mold is used with the evaporation and electroplating techniques to fabricate metal microneedle array device. This method greatly reduces the complexity of the fabrication and the cost of the material. The metal microneedle array electroplated on the polymer hollow microneedle array mold has a good rigidity and slant uniformity, and is suitable for mass production. The present invention may be widely used in blood sampling, micro-sampling and medication injection systems.

Although the present invention has been described with reference to the preferred embodiments, it will be understood that the invention is not limited to the details described thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A method of fabricating a microneedle array device, comprising the steps of:
    (1) providing a substrate, and forming a plurality of concave areas on a surface of said substrate;
    (2) coating a layer of photo-sensitive material on top of said substrate, and coating a layer of light transmission material on top of said photo-sensitive material;
    (3) using a patterned mask for exposure and development of said photo-sensitive material on said light transmission material to obtain a polymer hollow microneedle array mold using said light transmission material as a base; and
    (4) forming a microneedle array device using said polymer hollow microneedle array mold.

2. The method as claimed in claim 1, wherein said substrate in step (1) is made of silicon.

3. The method as claimed in claim 1, wherein said plurality of concave areas on said substrate in step (1) are formed by an etching technique.

4. The method as claimed in claim 3, wherein said etching technique is anisotropic wet etching technique.

5. The method as claimed in claim 1, wherein said plurality of concave areas on said substrate in step (1) are formed by X-ray etching, ultra-violet etching, ion beam etching, or excimer laser micromachining.

6. The method as claimed in claim 1, wherein said plurality of concave areas on said substrate in step (1) are formed by micro electro discharge machining technique.

7. The method as claimed in claim 1, wherein said photosensitive material in said step (2) is SU-8 or JSR430N.

8. The method as claimed in claim 1, wherein said light transmission material in said step (2) is PMMA or glass.

9. The method as claimed in claim 1, wherein said step (3) further comprises a step of using a patterned mask to define the shape of microneedles.

10. The method as claimed in claim 9, wherein said patterned mask comprises a plurality of pairs of closed curves, each said pair of closed curves comprise a first closed curve and a second closed curve, said first closed curve encompasses said second closed curve, said second closed curve has a circumference smaller than that of said first closed curve, and remaining areas are masked except the area between said first and said second closed curves.

11. The method as claimed in claim 9, wherein said step (3) further comprises a step of forming at least a reservoir layer.

12. The method as claimed in claim 11, wherein the shape of each said reservoir layer is defined by using a corresponding patterned mask.

13. The method as claimed in claim 11, wherein the depth of each said reservoir layer is controlled by adjusting exposure dosage of light.

14. The method as claimed in claim 1, wherein said step (4) further comprises the following sub-steps of:
   (4a) coating a metal layer on outer surfaces of said polymer hollow microneedle array mold and said light transmission material to form said microneedle array device; and
   (4b) removing said polymer hollow microneedle array mold from said microneedle array device.

15. The method as claimed in claim 14, wherein coating said metal layer in said step (4a) is by electroplating, electroless plating, evaporation, or sputtering.

16. The method as claimed in claim 14, wherein said metal layer is chosen from one of Cu, Cr, Ni, Fe, Au, Pt, Pd, stainless steel and their alloys.

17. The method as claimed in claim 14, wherein removing said polymer hollow microneedle array mold in said step (4b) uses one of oxygen removal, thermal removal, solvent removal, aqueous removal, photo-degradation removal, and their combinations.

* * * * *